(12) United States Patent
Grubac et al.

(10) Patent No.: US 10,376,690 B2
(45) Date of Patent: *Aug. 13, 2019

(54) INTERVENTIONAL MEDICAL SYSTEMS, DEVICES, AND COMPONENTS THEREOF

(71) Applicant: Medtronic, Inc., Minneapolis, MN (US)

(72) Inventors: Vladimir Grubac, Brooklyn Park, MN (US); Thomas A. Anderson, New Hope, MN (US); Jonathan L. Kuhn, Ham Lake, MN (US); Richard W. Swenson, Edina, MN (US); Michael P. Campbell, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 59 days.

This patent is subject to a terminal disclaimer.

(21) Appl. No.: 15/620,988

(22) Filed: Jun. 13, 2017

(65) Prior Publication Data

US 2017/0274202 A1 Sep. 28, 2017

Related U.S. Application Data

(63) Continuation of application No. 14/518,211, filed on Oct. 20, 2014, now Pat. No. 9,675,798.
(Continued)

(51) Int. Cl.
*A61N 1/05* (2006.01)
*A61N 1/375* (2006.01)
*A61N 1/362* (2006.01)

(52) U.S. Cl.
CPC ............. *A61N 1/057* (2013.01); *A61N 1/362* (2013.01); *A61N 1/3756* (2013.01)

(58) Field of Classification Search
CPC .......... A61N 1/05; A61N 1/057; A61N 1/362; A61N 1/3756; A61N 2001/0578; A61B 19/00; A61B 19/201; A61B 2019/208
See application file for complete search history.

(56) References Cited

U.S. PATENT DOCUMENTS 3,814,104 A 6/1974 Irnich et al.
3,835,864 A 9/1974 Rasor et al.
(Continued)

FOREIGN PATENT DOCUMENTS

WO 02071977 A2 9/2002
WO 2004028348 A2 4/2004
(Continued)

OTHER PUBLICATIONS (PCT/US2014/057596) PCT Notification of Transmittal of the International Search Report and the Written Opinion of the International Searching Authority, dated Dec. 5, 2014, 12 pages.
(Continued)

*Primary Examiner* — Vi X Nguyen

(57) ABSTRACT

A fixation member component, for example, employed by a relatively compact implantable medical device, includes a plurality of fingers; each finger includes a first segment extending from a fixed end of the corresponding finger, and a second segment extending from the corresponding first segment to a free end of the corresponding finger. Each first segment is elastically deformable from a relaxed to an extended condition, and from the relaxed to a compressed condition, and includes a peripheral portion and a central cut-out portion, framed by the peripheral portion. In the compressed condition, a free tip of the cut-out portion of some or all of the fingers may lodge against opposing tissue surfaces, via a spring force of the compressed fingers. Each second segment and cut-out portion is preferably configured
(Continued)

to prevent penetration thereof within tissue at the implant site.

33 Claims, 11 Drawing Sheets

Related U.S. Application Data

(60) Provisional application No. 62/041,940, filed on Aug. 26, 2014.

(56) References Cited

U.S. PATENT DOCUMENTS

| | | | |
|---|---|---|---|
| 3,902,501 | A | 9/1975 | Citron et al. |
| 4,103,690 | A | 8/1978 | Harris |
| 4,424,551 | A | 1/1984 | Stevenson et al. |
| 5,184,625 | A | 2/1993 | Cottone, Jr. et al. |
| 5,492,119 | A | 2/1996 | Abrams |
| 5,642,736 | A | 7/1997 | Avitall |
| 5,836,960 | A | 11/1998 | Kolesa et al. |
| 5,916,214 | A | 6/1999 | Cosio et al. |
| 6,152,144 | A | 11/2000 | Lesh et al. |
| 6,582,443 | B2 | 6/2003 | Cabak et al. |
| 6,716,238 | B2 | 4/2004 | Elliott |
| 6,941,169 | B2 | 9/2005 | Pappu |
| 7,149,587 | B2 | 12/2006 | Wardle et al. |
| 7,497,844 | B2 | 3/2009 | Spear et al. |
| 7,509,169 | B2 | 3/2009 | Eigler et al. |
| 7,515,971 | B1 | 4/2009 | Doan |
| 7,566,336 | B2 | 7/2009 | Corcoran et al. |
| 7,623,899 | B2 | 11/2009 | Worley et al. |
| 7,647,124 | B2 | 1/2010 | Williams |
| 8,032,220 | B2 | 10/2011 | Kuzma |
| 8,473,023 | B2 | 6/2013 | Worley et al. |
| 8,500,733 | B2 | 8/2013 | Watson |
| 8,634,919 | B1 | 1/2014 | Hou et al. |
| 8,795,328 | B2 | 8/2014 | Miles et al. |
| 9,119,959 | B2 | 9/2015 | Rys et al. |
| 9,155,882 | B2 | 10/2015 | Grubac et al. |
| 9,283,381 | B2 | 3/2016 | Grubac et al. |
| 9,526,522 | B2 | 12/2016 | Wood et al. |
| 9,675,798 | B2 * | 6/2017 | Grubac ................ A61N 1/3756 |
| 2002/0165537 | A1 | 11/2002 | Kelley et al. |
| 2002/0183823 | A1 | 12/2002 | Pappu |
| 2002/0183824 | A1 | 12/2002 | Borgersen et al. |
| 2004/0133089 | A1 | 7/2004 | Kilcoyne et al. |
| 2004/0147973 | A1 | 7/2004 | Hauser |
| 2004/0215307 | A1 | 10/2004 | Michels et al. |
| 2005/0004602 | A1 | 1/2005 | Hart et al. |
| 2005/0004641 | A1 | 1/2005 | Pappu |
| 2005/0004644 | A1 * | 1/2005 | Kelsch ............... A61B 17/8888 607/131 |
| 2005/0136385 | A1 | 6/2005 | Mann et al. |
| 2006/0247753 | A1 | 11/2006 | Wenger et al. |
| 2007/0083230 | A1 | 4/2007 | Javois |
| 2007/0156114 | A1 | 7/2007 | Worley et al. |
| 2007/0219590 | A1 | 9/2007 | Hastings |
| 2008/0057100 | A1 | 3/2008 | Williams et al. |
| 2010/0094314 | A1 | 4/2010 | Hernlund et al. |
| 2010/0228279 | A1 | 9/2010 | Miles et al. |
| 2010/0274227 | A1 | 10/2010 | Khairkhahan et al. |
| 2011/0144572 | A1 | 6/2011 | Kassab et al. |
| 2011/0251660 | A1 | 10/2011 | Griswold |
| 2012/0059448 | A1 | 3/2012 | Parker et al. |
| 2012/0172690 | A1 | 7/2012 | Anderson et al. |
| 2012/0172892 | A1 | 7/2012 | Grubac et al. |
| 2012/0197373 | A1 | 8/2012 | Khairkhahan et al. |
| 2013/0035748 | A1 | 2/2013 | Bonner et al. |
| 2013/0079798 | A1 | 3/2013 | Tran et al. |
| 2013/0103047 | A1 * | 4/2013 | Steingisser .......... A61N 1/3756 606/129 |
| 2013/0131591 | A1 | 5/2013 | Berthiaume et al. |
| 2013/0131693 | A1 | 5/2013 | Berthiaume et al. |
| 2013/0253347 | A1 | 9/2013 | Griswold et al. |
| 2015/0039070 | A1 | 2/2015 | Kuhn et al. |
| 2015/0051611 | A1 | 2/2015 | Schmidt et al. |
| 2015/0253347 | A1 | 9/2015 | Cong et al. |
| 2015/0352353 | A1 | 12/2015 | Rys et al. |
| 2016/0015322 | A1 | 1/2016 | Anderson et al. |
| 2016/0059003 | A1 | 3/2016 | Eggen et al. |

FOREIGN PATENT DOCUMENTS

| | | |
|---|---|---|
| WO | 2005034764 A1 | 4/2005 |
| WO | 2013043671 A1 | 3/2013 |
| WO | 2013062793 A1 | 5/2013 |
| WO | 2015017157 A1 | 2/2015 |

OTHER PUBLICATIONS (PCT/US2014/057727) PCT Notification of Transmittal of the International Search Report and the Written Opinion of the International Searching Authority, dated Dec. 8, 2014, 12 pages.
(PCT/US2015/040870) PCT Notification of Transmittal of the International Search Report and the Written Opinion of the International Searching Authority, dated Oct. 14, 2015, 10 pages.
(PCT/US2015/043957) PCT Notification of Transmittal of the International Search Report and the Written Opinion of the International Searching Authority, dated Nov. 11, 2015, 9 pages.
Prosecution History from U.S. Appl. No. 14/518,211, dated from May 19, 2016 through Feb. 6, 2017, 42 pp.

* cited by examiner

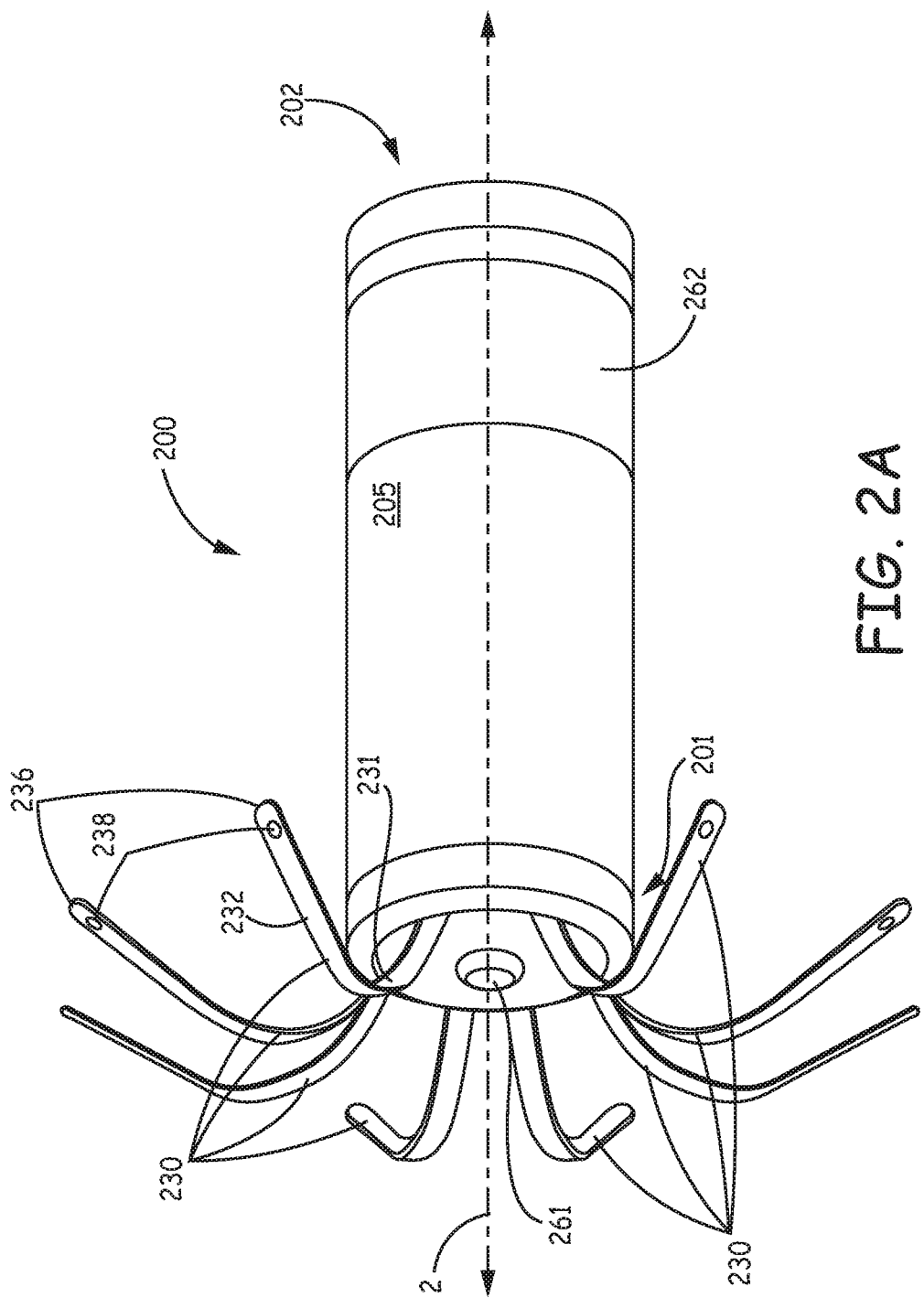

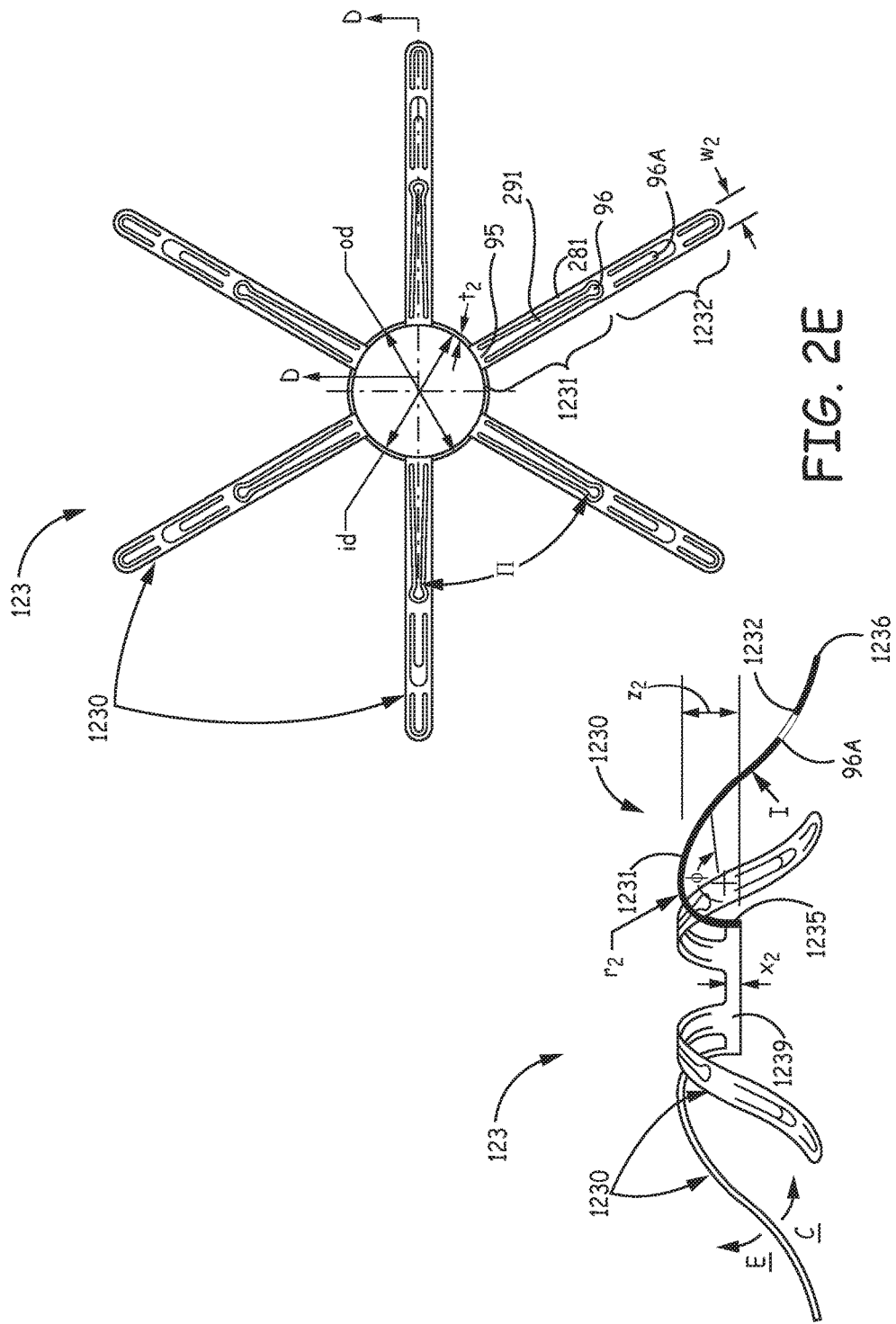

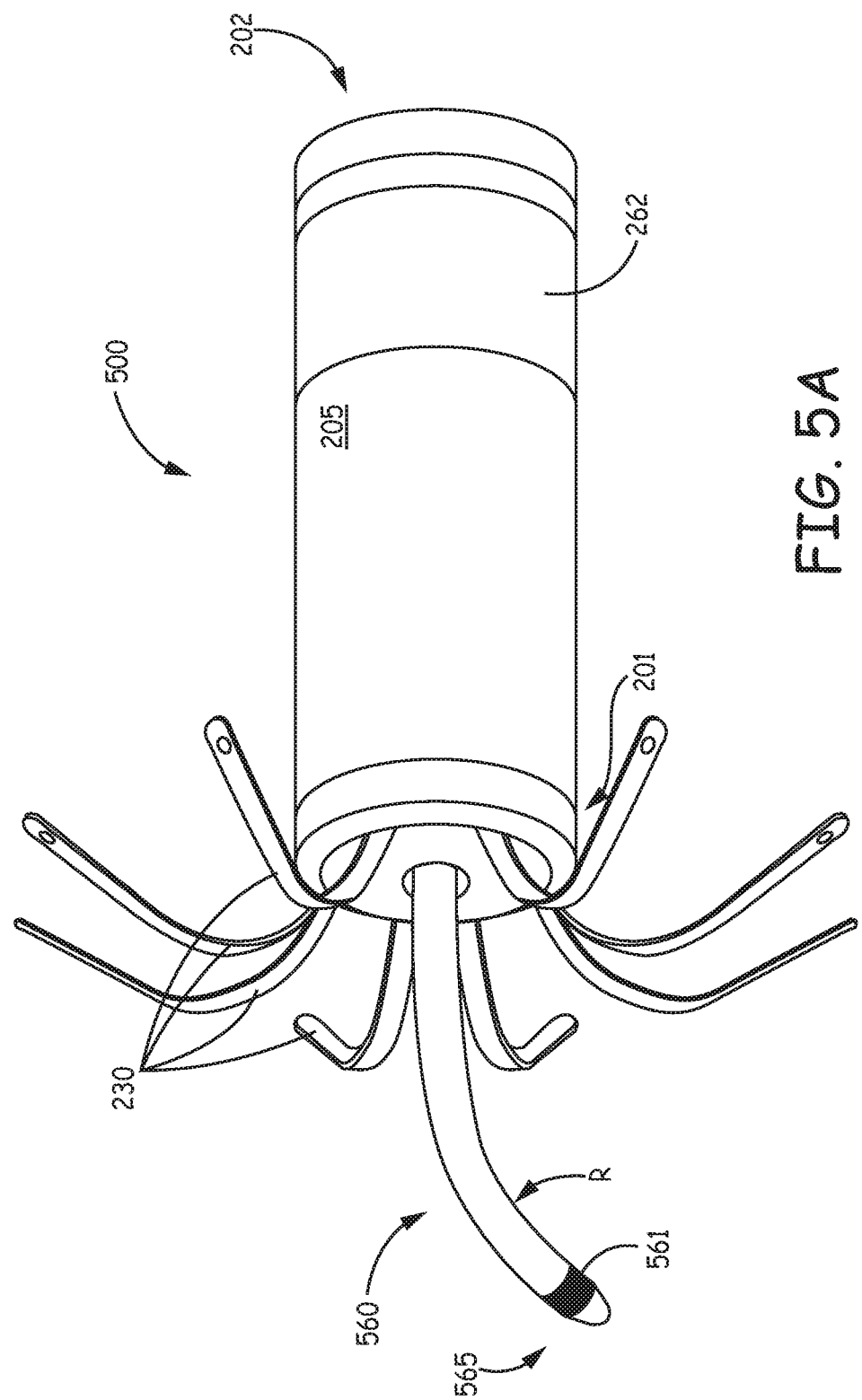

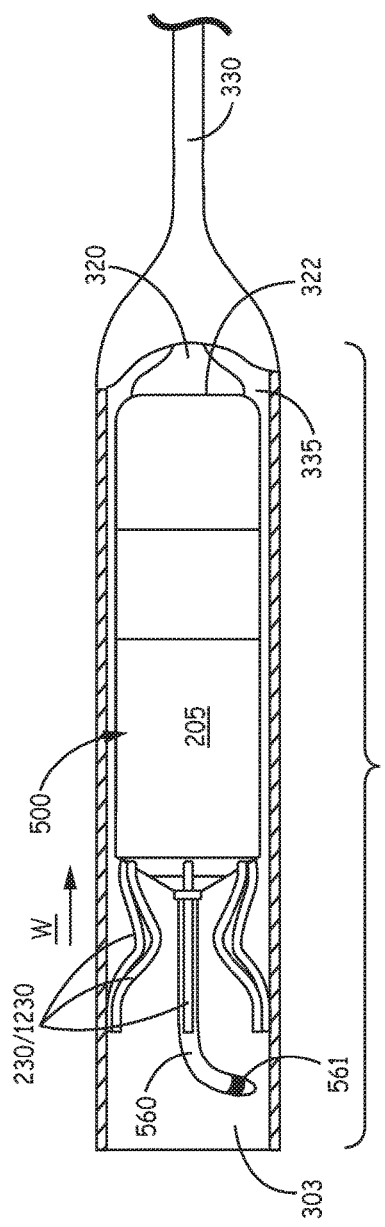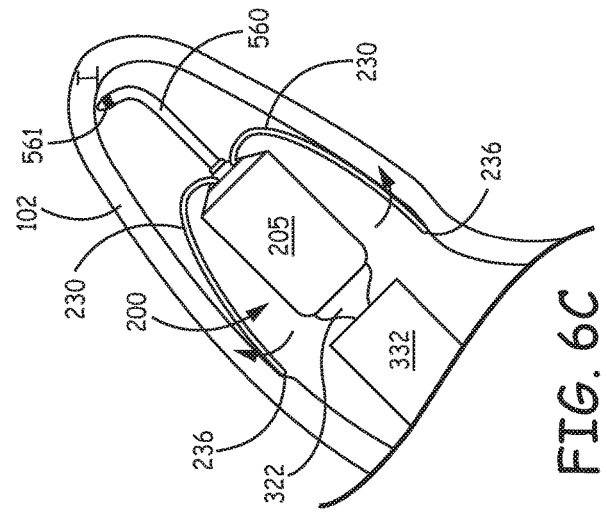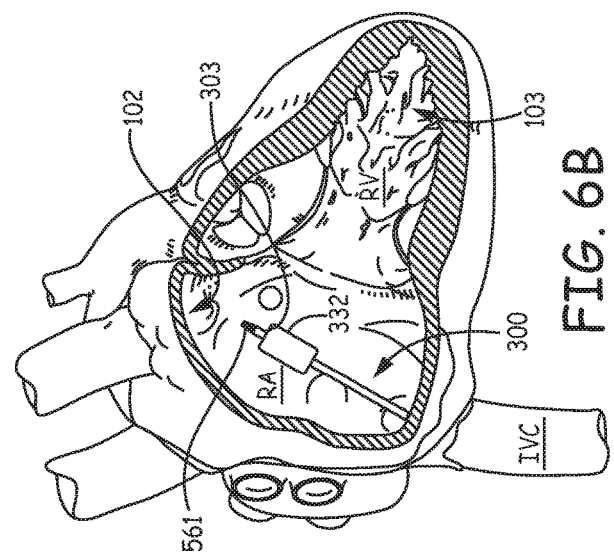

INTERVENTIONAL MEDICAL SYSTEMS, DEVICES, AND COMPONENTS THEREOF

CROSS-REFERENCE TO RELATED APPLICATION

This application is a continuation of U.S. patent application Ser. No. 14/518,211 (now allowed), filed Oct. 20, 2014 entitled "INTERVENTIONAL MEDICAL SYSTEMS, DEVICES, AND COMPONENTS THEREOF", which is herein incorporated by reference in its entirety.

The present application also claims priority to the United States Provisional Patent Application having the Ser. No. 62/041,940, which was filed on Aug. 26, 2014 and is hereby incorporated by reference in its entirety. The present application is related to the co-pending and commonly assigned U.S. patent application, Ser. No. 14/518,261, filed Oct. 20, 2014, entitled INTERVENTIONAL MEDICAL SYSTEMS, DEVICES, AND METHODS OF USE, and which is incorporated by reference in its entirety.

FIELD OF THE DISCLOSURE

The present disclosure pertains to interventional medical systems, and more particularly to relatively compact implantable medical devices thereof and associated components.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV. An implanting physician may employ a standard guiding catheter (not shown) to deliver a relatively compact medical device to any one of the three exemplary sites, for example, according to methods known in the art of interventional cardiology, by maneuvering the catheter, with the device loaded therein, up through the inferior vena cava IVC and into the right atrium RA. However, a co-pending and commonly assigned U.S. patent application having the Ser. No. 14/039,937 discloses a more sophisticated delivery tool, which the operator may employ, in lieu of the standard guiding catheter, to deliver and to fix the device at the desired implant site.

SUMMARY

A relatively compact implantable medical device, according to embodiments disclosed herein, includes a fixation member formed by a plurality of fingers mounted around a perimeter of a distal end of a housing of the device, wherein each finger includes a first segment extending from a fixed end of the corresponding finger, and a second segment extending from the corresponding first segment to a free end of the corresponding finger. The first segment of each finger is elastically deformable from a relaxed condition to an extended condition, and from the relaxed condition to a compressed condition, and each first segment includes a peripheral portion and a central cut-out portion, which is framed by the peripheral portion so that an inside edge of the peripheral portion is spaced apart from an outside edge of the central cut-out portion. The central cut-out portion of the first segment of each finger extends from a fixed end thereof to a free tip thereof, wherein the fixed end is integral with the peripheral portion and located in proximity to the fixed end of the corresponding finger. The second segment of each finger extends in a proximal direction and outward from the device housing, when the corresponding first segment is in the relaxed condition, and extends distally from the distal end of the device housing, when the corresponding proximal end is in the extended condition. According to some embodiments, the second segment of each finger may also include at least one peripheral portion and corresponding central cut-out portion. A fixation member component, according to some embodiments, includes the above described plurality of fingers integrally formed with a base ring, wherein the fixed end of each fingers is joined to the base ring.

According to some system embodiments disclosed herein, a delivery tool contains an entirety of the device while holding the first segment of each of the fixation fingers thereof in the extended condition, to deliver the device to a target implant site. Once in proximity to the site, the tool may be manipulated to expose the fixation fingers and thereby release the first segment of each to the relaxed condition, after which the tool and device together may be advanced to the site thereby wedging the exposed fingers between opposing tissue surfaces so that the first segment of each is in the compressed condition. In the compressed condition, the free tip of the above-described central cut-out portion(s) of some or all of the fixation fingers may catch, or lodge against opposing tissue surfaces, via a spring force of the compressed fingers, to provide fixation for the implanted device. The second segment and each central cut-out portion of each fixation finger is preferably configured to prevent penetration thereof within tissue at the implant site.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 2A is a perspective view of an implantable medical device, according to some embodiments;

FIGS. 2D-E are elevation and end views of another exemplary fixation member component which may be employed by the device of FIG. 2, according to some alternate embodiments;

FIG. 5A is a perspective view of an implantable medical device, according to some additional embodiments;

FIGS. 6A-C are schematics according to some alternate methods of the present invention.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
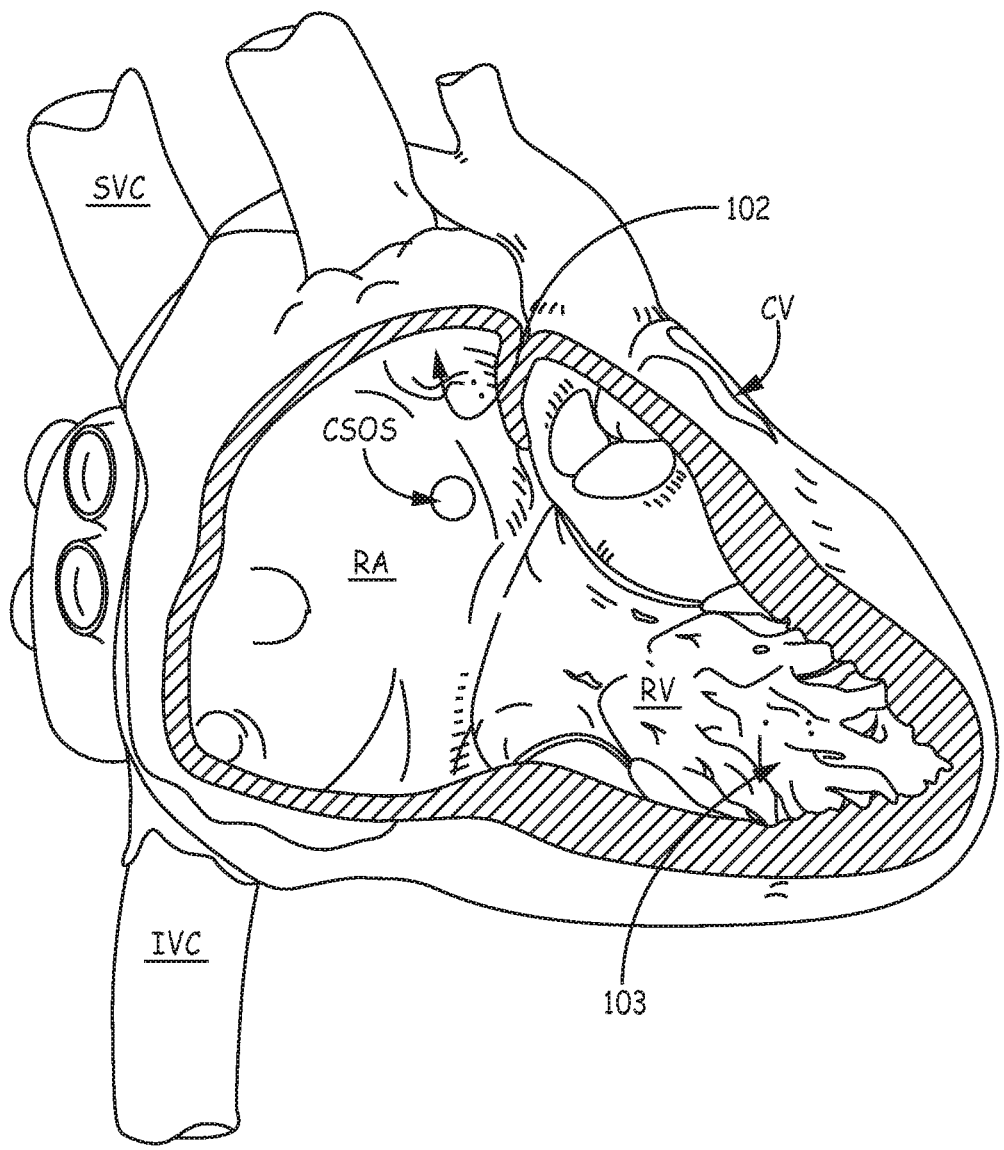
FIG. 1 is a schematic diagram showing potential implant sites for embodiments of the present invention.

FIG. 2A is a perspective view of an implantable medical device 200, according to some embodiments. FIG. 2A illustrates device 200 including a hermetically sealed housing 205, preferably formed from a biocompatible and biostable metal such as titanium, which contains a pulse generator (e.g., a power source and an electronic controller—not shown), a fixation member, which is formed by a plurality of fixation fingers 230 spaced apart from one another around a perimeter of a distal end 201 of housing 205, and an electrode 261, which is located at the distal end 201 of housing 205 being coupled to the controller of device 200 by a hermetic feedthrough assembly (not shown) constructed according to those known to those skilled in the art of implantable medical devices. Housing 205 may be overlaid with an insulative layer, for example, medical grade polyurethane, parylene, or silicone, and FIG. 2A further illustrates another electrode 262 of device 200, which may be formed by removing a portion of the insulative layer to expose the metallic surface of housing 205. According to the illustrated embodiment, electrode 262 may function in conjunction with electrode 261 for bipolar pacing and sensing, when fixation fingers 230 hold electrode 261 in intimate tissue contact at a target implant site, for example, within right atrial appendage 102 or within right ventricle RV in proximity to apex 103 (FIG. 1). Fixation fingers 230 function to hold device 200 at the implant site by being wedged between opposing tissue surfaces at the site.

Figure 2C:
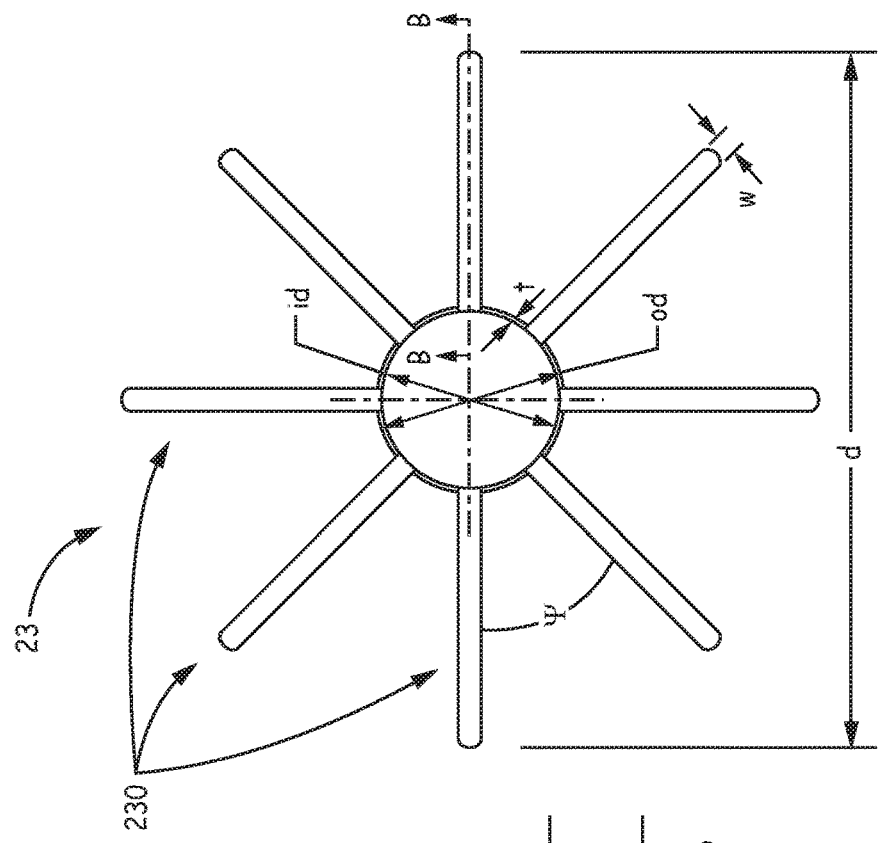
FIGS. 2B-C are elevation and end views of an exemplary fixation member component which may be employed by the device of FIG. 2, according to some embodiments.
Figure 2B:
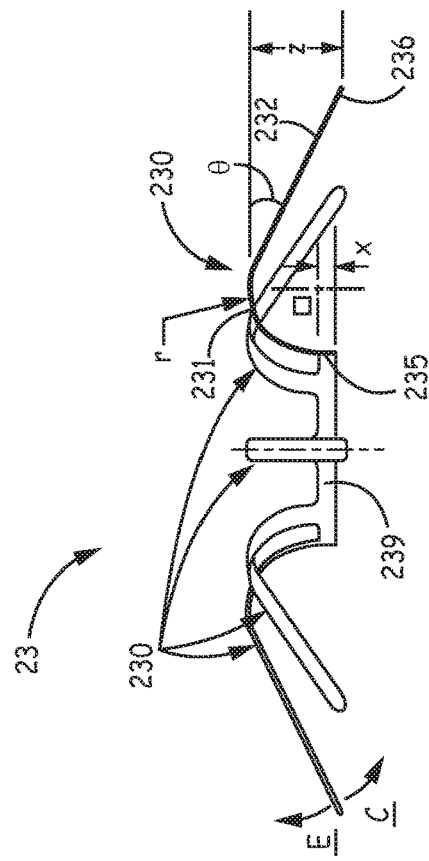

FIGS. 2B-C are elevation and end views of an exemplary fixation member component 23 which may be employed by device 200, according to some embodiments. FIGS. 2B-C illustrate fixation member component 23 including eight fixation fingers 203 integrally formed with one another and a base ring 239, such that a thickness t of base ring 239 is approximately the same as that of each finger 230. According to an exemplary embodiment, fixation member component 23 is cut from Nitinol tubing, according to methods known in the art, and thickness t may be 0.005 inch +/- 0.001 inch, wherein base ring 239 may have an inner diameter id of approximately 0.20 inch and an outer diameter od of approximately 0.21 inch. A height x of base ring 239 may be approximately equal to a width w of each finger, for example, approximately 0.024 inch. After cutting the aforementioned Nitinol tubing, fingers 230 are shaped by bending and holding fingers 230 in the illustrated curvature while heat treating component 23 according to methods known to those skilled in the art. FIG. 2B illustrates (via cross-section through section line B-B of FIG. 2C) each fixation finger 230 including a first segment 231 and a second segment 232, wherein each first segment 231 extends from a fixed end 235 of the corresponding finger 230 to the corresponding second segment 232, and each second segment 232 extends from the corresponding first segment 231 to a free end 236 of the corresponding finger 230. FIGS. 2A-B further illustrates each first segment 231, in a relaxed condition, extending in an arc, distally and outwardly from fixed end 235, and second segment 232 extending from first segment 231 in a proximal direction and outward from device housing 205. With further reference to FIG. 2C fixation fingers 230 are spaced equally apart from one another such that an angle ψ defined between each adjacent pair is approximately 45 degrees. Component 23 may be mounted to distal end 201 of device housing 205, for example, in a manner similar to that described for a fixation component 102 in co-pending and commonly assigned United States Patent Application 2012/0172690, which description is hereby incorporated by reference.

Figure 3:
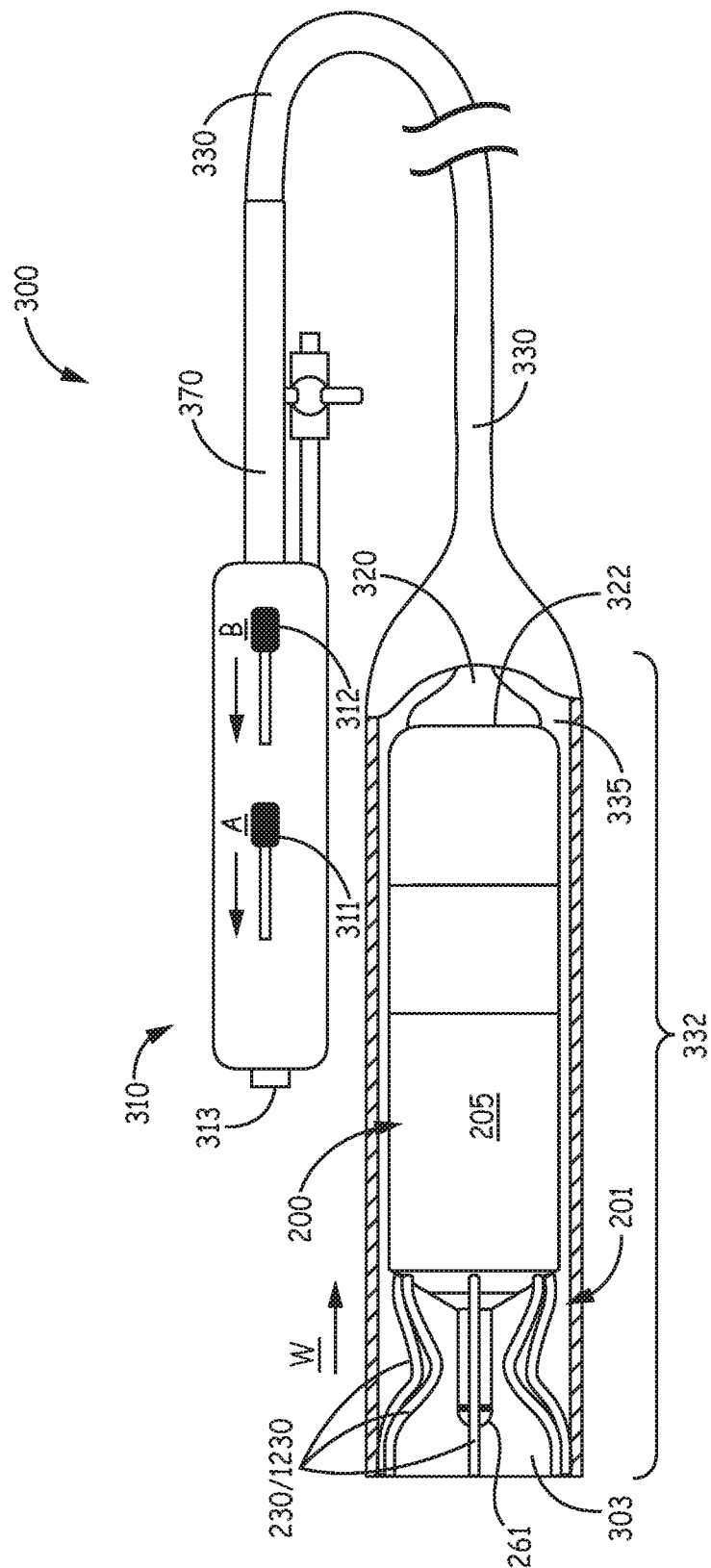
FIG. 3 is a plan view of an interventional medical system with a partial cut-away section, according to some embodiments.
Figure 4A:
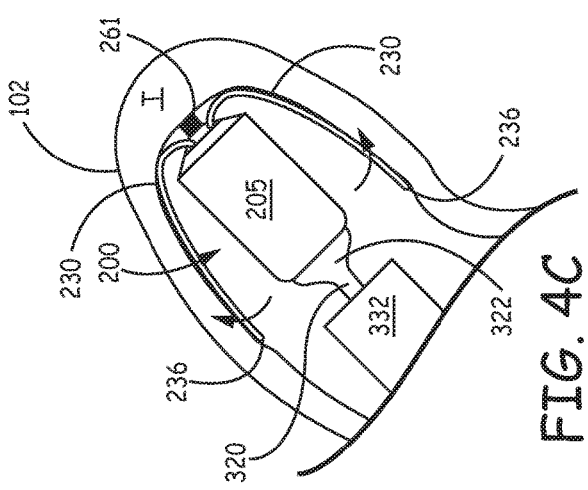
FIGS. 4A-D are schematics outlining some methods of the present invention.
Figure 4B:
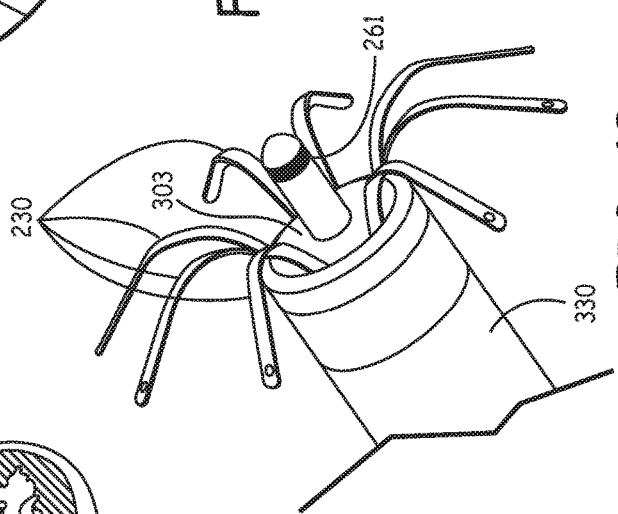

According to the illustrated embodiment, first segment 231 of each fixation finger 230 is elastically deformable between the relaxed condition and an extended condition, per arrow E of FIG. 2B, and between the relaxed condition and a compressed condition, per arrow C of FIG. 2B. The extended condition is described below in conjunction with FIGS. 3, 4A, and 6A-B; and the compressed condition is described below in conjunction with FIGS. 4C and 6C. With further reference to FIG. 2B, the angle enclosed by the arc of first segment 231 of each finger 230 is shown being at least 90 degrees, with second segment 232 extending away from first segment 231 at an angle θ. According to an exemplary embodiment, a radius r of the arc of each first segment 231 is approximately 0.067 inch, and angle θ is approximately 26 degrees. FIG. 2B further illustrates each second segment 232 extending in a proximal direction from first segment 231 over a distance just slightly greater than a distance z, wherein distance z may be approximately 0.095 inch measured from a proximal edge of base ring 239 to a tangent line extending from an intersection of first and second segments 231, 232. Although not shown in FIG. 2A, according to some preferred embodiment, electrode 261 may be mounted on a relatively short extension formed in distal end 201 of housing 205 such that electrode 261 is spaced distal to radius r of each finger 230, for example, as shown in FIGS. 3 and 4B, wherein the distance from the apex of radius r to the distally spaced electrode 261 may be approximately 2 mm.

FIGS. 2D-E are elevation and end views of another exemplary fixation member component 123 which may be employed by device 200 in lieu of component 23, according to some alternate embodiments. FIGS. 2D-E illustrate fixation member component 123 including six fixation fingers 1203 integrally formed with one another and a base ring 1239, such that a thickness t2 of base ring 1239 is approximately the same as that of each finger 1230. Fixation fingers 1230 are shown spaced equally apart from one another such that an angle π defined between each adjacent pair is approximately 60 degrees. A height x2 of base ring 1239 may be approximately 0.02 inch and a width w2 of each finger 1230 may be approximately 0.05 inch. FIGS. 2D-E further illustrate each finger 1230 including a first segment 1231 and a second segment 1232, similar to fingers 230 of component 23, wherein each first segment 1231 extends from a fixed end 1235 of the corresponding finger 1230 to the corresponding second segment 1232, and each second segment 1232 extends from the corresponding first segment 1231 to a free end 1236 of the corresponding finger 1230. In contrast to fingers 230 of component 23, first segment 1231 of each finger 1230 includes a peripheral portion 281 and a central cut-out portion 291, which is framed by peripheral portion 281, as is best seen in the enlarged plan view of one of fingers 1230 in FIG. 2F.

With further reference to FIG. 2D, first segment 1231, in a relaxed condition, is shown (via cross-section through section line D-D of FIG. 2E) extending in a compound curve (e.g., having two radii of curvature, a first being approximately 0.065 inch and a second being approximately 0.29 inch), distally and outwardly from the corresponding fixed end 1235, and second segment 1232 is shown extending from first segment 1231 in a proximal direction and outward from base ring 1239. According to the illustrated embodiment, first segment 1231 of each fixation finger 1230 is elastically deformable between the relaxed condition and an extended condition, per arrow E of FIG. 2D, and between the relaxed condition and a compressed condition, per arrow C of FIG. 2D. The extended condition is described below in conjunction with FIGS. 3, 4A, and 6A-B; and the compressed condition is described below in conjunction with FIG. 4D. With further reference to FIG. 2D, the compound curve of first segment 1231 of each finger 230 encloses an angle φ that is between approximately 135 degrees and 180 degrees, and, according to an exemplary embodiment, a radius r2 of a first portion of the compound curve is approximately 0.065 inch, and a distance z2 from a proximal edge of base ring 1239 to an apex of the first portion of the compound curve is approximately 0.095 inch. Second segment 1232 of each finger 230 may extend along a radius of curvature in an opposite direction, for example, being approximately 0.29 inch, and starting at an inflection point I, which is designated in FIG. 2D.

Figure 2F:
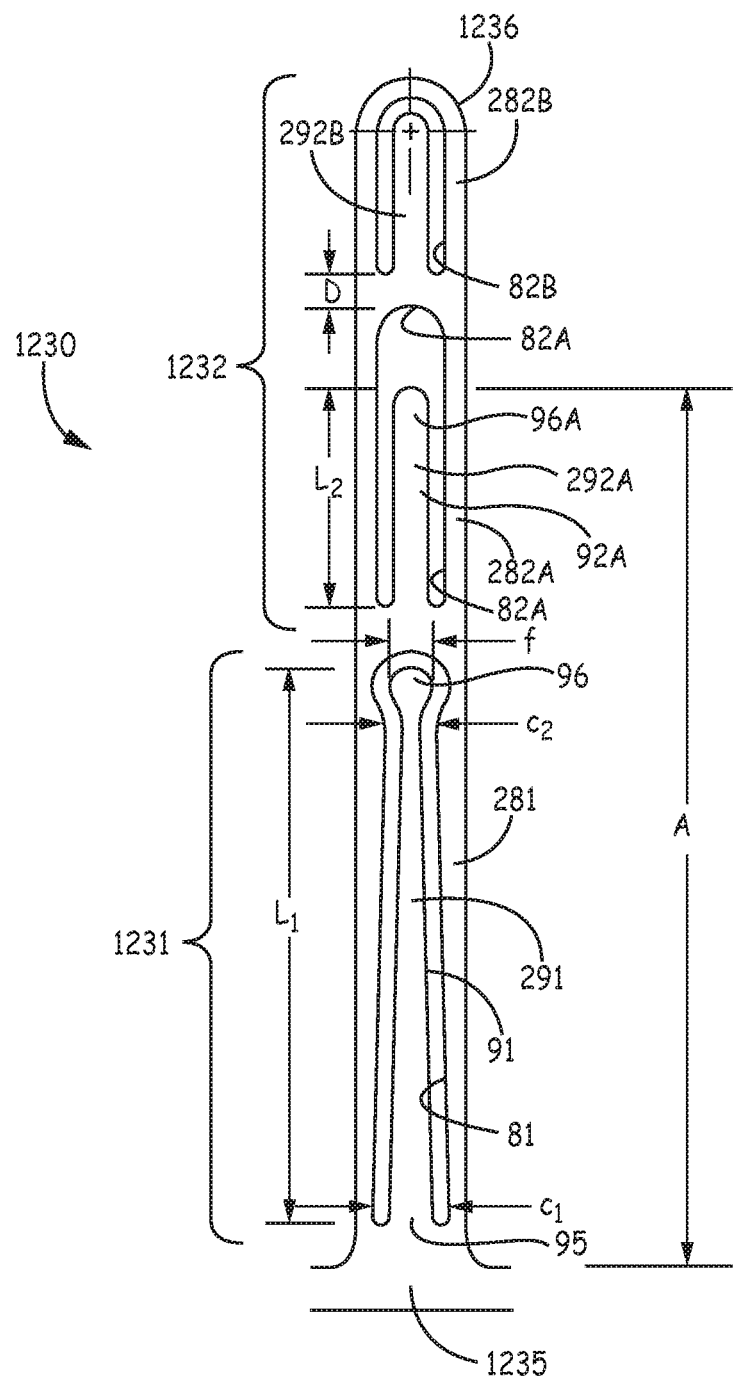
FIG. 2F is an enlarged plan view of a finger of the fixation member component of FIGS. 2D-E, according to some alternate embodiments.

FIG. 2F illustrates peripheral portion 281 of first segment 1231, which may be likened to a strut, framing central cut-out portion 291 so that an inside edge 81 of peripheral portion 281 is spaced apart from an outside edge 91 of central cut-out portion 291. FIGS. 2E-F further illustrate each central cut-out portion 291 extending from a fixed end 95 thereof to a free tip 96 thereof, wherein fixed end 95 is integral with the corresponding peripheral portion 281 and located in proximity to fixed end 1235 of the corresponding finger 1230. With reference to FIG. 2F, a length L1 of central cut-out portion 291 extends along a majority of the length of first segment 1231 and may be approximately 0.25 inch, according to some exemplary embodiments. FIG. 2F further illustrates central cut-out portion 291 tapering from a first width c1, at fixed end 95, to a second width c2, in proximity to free tip 96, wherein first width c1 is greater than second width c2; and free tip 96 is shown being rounded and having a width f greater than second width c2.

With further reference to FIGS. 2D-F, according to some embodiments, second segment 1232 of each finger 1230 includes two peripheral portions 282A, 282B, each framing a corresponding central cut-out portion 292A, 292B, which are spaced apart from one another along a length of second segment 1232. According to the illustrated embodiment, a width of each central cut-out portion 292A, 292B is constant along the corresponding length thereof, for example, being approximately 0.018 inch. A free tip 96A of each central cut-out portion 292A is preferably located along the aforementioned curvature of the corresponding second segment 1232, as may be seen in FIG. 2D, for example, such that a distance A (FIG. 2F) between each free tip 96A and fixed end 1235 of the corresponding finger 1230 may be approximately 0.4 inch, wherein a length L2 of each portion 292A may be approximately 0.1 inch. The other, distal-most, central cut-out portion 292B of each finger 1230 is relatively shorter and located in close proximity to the corresponding free end 1236, for example, to reduce a stiffness of each finger 1230 at the free end 1236 thereof, and thereby preventing tissue penetration. With further reference to FIG. 2F, a distance D between an inner edge 82A of peripheral portion 282A and central cut-out portion 292B can dictate a stiffness of portion 292B (the smaller D, the less stiff portion 292B), and, according to some exemplary embodiments, distance D is approximately 0.015 inch.

Fixation member component 123, like component 23, may be cut from Nitinol tubing, according to methods known in the art, and thickness t2 may be 0.005 inch +/− 0.001 inch, wherein base ring 1239 may have the same inner diameter id (approximately 0.20 inch) and outer diameter od (approximately 0.21 inch) as base ring 239 of component 23, for example, being sized for mounting around a perimeter of device housing 205, in lieu of component 23 and in a similar manner to that described in the above-referenced application '690. After cutting the Nitinol tubing, fingers 1230 are shaped by bending and holding fingers 1230 in the illustrated curvature while heat treating component 123 according to methods known to those skilled in the art.

FIG. 3 is a plan view of an interventional medical system with a partial cut-away section, according to some embodiments, wherein the system includes a delivery tool 300, in which device 200 is loaded, for deploying device 200 to a target implant site. FIG. 3 illustrates tool 300 including a handle 310, an elongate inner member 320, and an outer assembly, which is formed by an elongate deployment tube 330 and an outer, stabilizing sheath 370 that is secured to handle 310 and surrounds a proximal portion of deployment tube 330 in proximity to handle 310. According to the illustrated embodiment, elongate inner member 220 extends within a lumen 335 of deployment tube 330, and a proximal end of deployment tube 330 is coupled to a control member 312 of handle 310 such that an entirety of deployment tube 330 is movable with respect to the inner member 320, via control member 312. FIG. 3 further illustrates inner member 320 including a distal end 322, which is located within a distal-most portion 332 of deployment tube 330, and which is configured to engage implantable medical device 200 by abutting proximal end 202 of device housing 205, as shown.

With further reference to FIG. 3, that portion of deployment tube lumen 335 which extends along a length of distal-most portion 332 is sized to contain distal end 322 of inner member 320 together with an entirety of device 200. FIG. 3 shows fixation fingers 230/1230 of the loaded device 200 being held by distal-most portion 332 in the aforementioned extended position. With reference to FIG. 4A, a distal portion of tool 300, with an entirety of device 200 loaded in distal-most portion 332, may be navigated to a target implant site, for example, in the right atrium RA (or right ventricle RV), by advancing tool 300 through a venous system of the patient, for example, from a femoral venous access site and up through the inferior vena cava IVC. A length of deployment tube 330, between handle 310 and a distal opening 303 of deployment tube 330, when tube 330 is in the position shown in FIG. 3, may be between approximately 103 cm and approximately 107 cm, for example, to reach the right atrium RA from the femoral access site. According to some embodiments of the present invention, delivery tool 300 includes articulating features to facilitate the navigation of the distal portion of delivery tool 300; for example, inner member 320 of delivery tool 300 may include a pull wire (not shown) integrated therein and coupled to another control member 311 of handle 310 that, when moved per arrow A, causes inner member 320 and deployment tube 330 to bend along distal portions thereof.

Suitable construction detail for a delivery tool like tool 300 is described in co-pending and commonly assigned U.S. patent application, Ser. No. 14/039,937, the description of which is hereby incorporated by reference.

According to some methods of the present invention, once an operator has located distal-most portion 332 in a chamber of the heart, for example, the right atrium RA, as shown in FIG. 4A, the operator can retract deployment tube 330, per arrow W (FIG. 3), for example, by moving control member 312 per arrow B (FIG. 3), to release fixation fingers 230/1230 to the relaxed position. Fingers 230 are shown in FIG. 4B, but if fingers 1230 were substituted for fingers 230, the relaxed position thereof would be like that shown in FIG. 2D. FIG. 4B illustrates each finger 230 having been exposed out through distal opening 303 of deployment tube 330 so that, in the relaxed position, each finger 230 extends in a proximal direction and outward from device housing 205. After releasing device fixation fingers 230/1230, the operator may advance tool 300 and device 200 together to a target implant site between folds of tissue, for example, pectinate muscle bands in right atrial appendage 102, and, thus, wedge the exposed fixation fingers 230/1230 between opposing tissue surfaces as shown schematically in FIGS. 4C-D. It should be noted that, with further reference to FIG. 4A, an alternate implant site may be in the right ventricle RV, where fixation fingers 230 may be wedged between folds of tissue (trabeculae) in the area of apex 103.

Figure 4C:
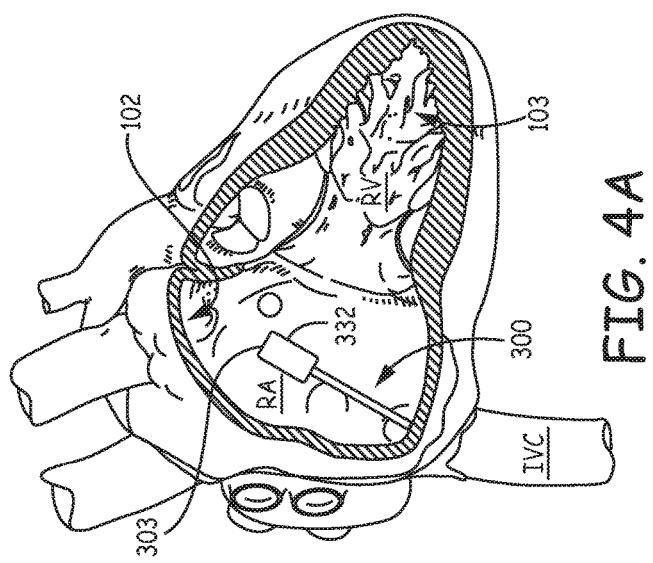
Figure 4D:
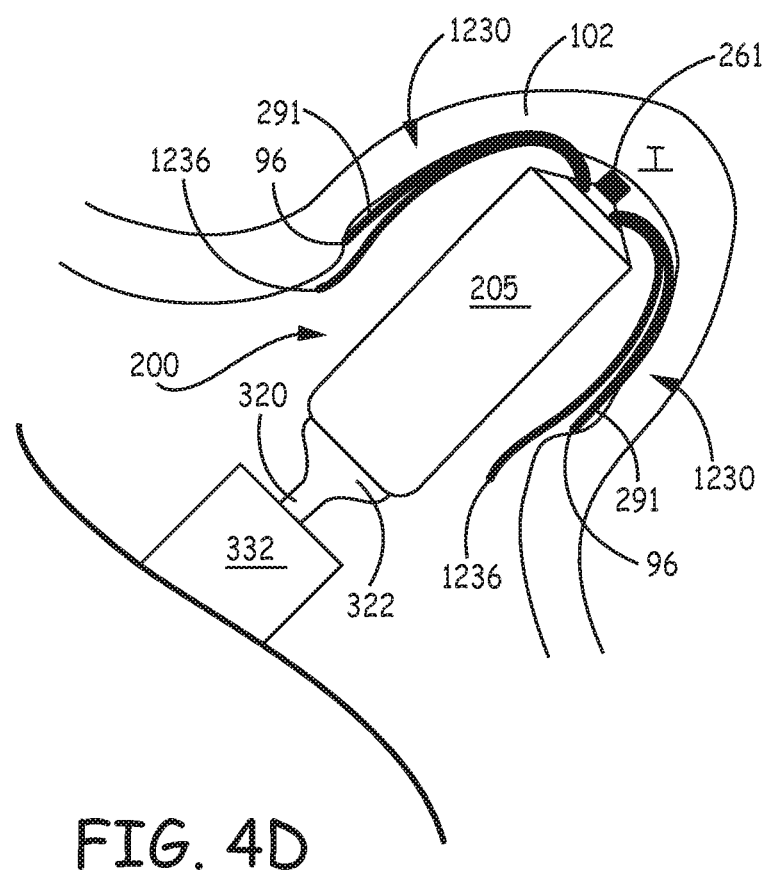

With reference to FIGS. 4C-D, distal end 322 of device inner member 320 may be employed to provide a push force that assists in wedging fingers 230/1230 so that fingers 230/1230 are in the aforementioned compressed state to hold electrode 261 in intimate tissue contact. The compressed fingers 230/1230, having a super-elastic nature, hold device 200 in place at the implant site by a spring force (per the bold arrows of FIG. 4C), and that finger free ends 236/1236 are preferably configured to prevent penetration thereof within tissue at the implant site, while merely catching, or lodging against opposing tissue surfaces. The inclusion of distal-most central cut-out portion 292B in each finger 1230, as was described above in conjunction with FIG. 2F, is an example of a configuration that can prevent finger penetration. With reference back to FIG. 2, according to some embodiments, one or more of finger free ends 236 includes a discrete radiopaque marker 238 attached thereto, for example, a platinum-iridium rivet like member, that may assist the operator in assessing the fixation of device 200 at the implant site. Furthermore, it should be noted that the fixation fingers 230 or 1230, as described above in conjunction with FIGS. 2B-F, may also be formed from a polymer material, either individually or integrally with the corresponding base ring 239, 1239, wherein an appropriate polymer material and associated dimensional specifications essentially mimics that of fingers 230, 1230 formed from the aforementioned Nitinol, in terms of spring properties.

With reference to FIG. 4D, fixation fingers 1230, substituted for fingers 230 in device 200, may be more effective to hold electrode 261 and device 200 in place when a depth of the fold, or crease between opposing tissue surfaces at the implant site is relatively shallow. A variety of depths may be encountered depending upon anatomical variation from patient to patient or from one potential implant site to another within a particular patient. FIG. 4D illustrates free tips 96 of central cut-out portions 291 of opposing fingers 1230, in the compressed condition, catching, or lodging against opposing tissue surfaces in a fold of tissue that may not be deep enough to accommodate a full length of fingers 230. But, even in a deeper crease or fold, the configuration of each finger 1230, according to some embodiments, provides multiple free ends or tips per finger to catch, or lodge against opposing tissue surfaces for enhanced fixation when finger 1230 is in the compressed condition. As was described above, in conjunction with FIG. 2F, in these embodiments, second segment 1232 of each finger 1230 includes central cut-out portion 292A and corresponding peripheral portion 282A, which may provide potential for a greater force of fixation for device 200 at an implant site, if the depth thereof between folds of tissue is sufficient for free tip 96A of portion 292A to catch, or lodge against the opposing tissue surfaces when fingers 1230 are wedged therebetween.

With further reference to FIG. 2F, the above-described tapering configuration of each central cut-out portion 291, in conjunction with the enlarged free tip 96 thereof, helps to prevent the penetration thereof into tissue at the implant site; furthermore, the configuration may enhance a fatigue life of fingers 1230 during chronic implantation of device 200 with fingers 1230 in the compressed condition. Furthermore, it should be noted that the fixation provided by fingers 1230 may be more aggressive if a spacing between outer edges 91, 92A and corresponding inner edges 81, 82A is relatively large. But more aggressive fixation may lead to more tissue in-growth over time and, thus, more difficulty in extracting device 200 after chronic implantation, therefore, a relatively smaller spacing between the aforementioned edges may be desired to provide a balance of adequate fixation and ease of chronic extraction. It is contemplated that one or more of inner edges 81, 82A, 82B of each finger 1230 could be tailored to cut through tissue in-growth as device 200 is extracted. It should also be noted that if the exemplary dimensions presented above in conjunction with FIGS. 2B-F are scaled down, for example, in proportion to a smaller overall implantable device volume, they will still fall within the scope of embodiments of the present invention.

Returning now to FIGS. 4C-D, after wedging fingers 230/1230 between opposing tissue surfaces, the operator may evaluate pacing performance of electrode 261 before completely withdrawing delivery tool 300 away from the implanted device 200. Thus, if the operator determines that the performance is not satisfactory, the operator may advance distal-most portion 332 of deployment tube 330 back in a distal direction, for example, via control member 312 (FIG. 3), relative to device 200 and inner member 320, and over wedged fixation fingers 230/1230 to move device 200 back into distal-most portion 332 with fingers 230/1230 moved back into the extended condition, as shown in FIG. 3. Then the operator can move delivery tool 300 with the re-loaded device 200 into proximity with an alternative implant site, retract deployment tube 330 again to expose and release fingers 230/1230 into the relaxed condition (FIG. 4B), and then advance tool 300 toward the other site to wedge the exposed fingers 230/1230 between opposing tissue surfaces at the other site.

Figure 5B:
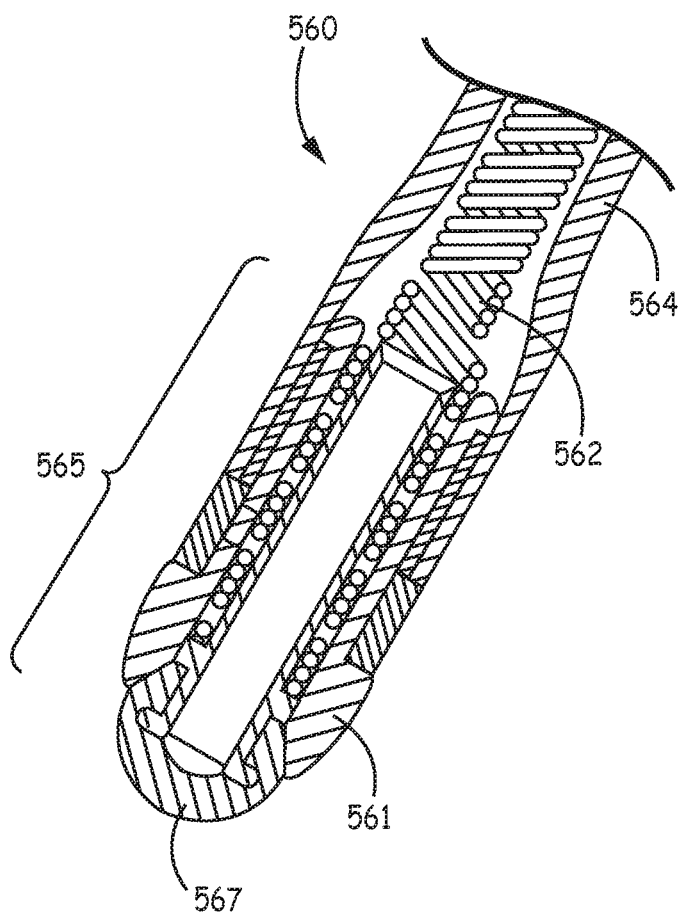
FIG. 5B is a cross-section view through a portion of the device of FIG. 5A, according to an exemplary construction of some embodiments.

FIG. 5A is a perspective view of an implantable medical device 500, according to some additional embodiments; and FIG. 5B is a cross-section view through a portion of device 500, according to an exemplary construction of some embodiments. FIG. 5A illustrates device 500 being similar to device 200 but including a pacing extension 560 on which a pacing electrode 561 is mounted, in lieu of electrode 261 of device 200. FIG. 5A further illustrates extension 560 including a preformed curvature located in proximity to, and proximal to electrode 561. A diameter of extension 560 may be approximately 0.05 inch (1.3 mm); an overall length of extension 560 may be approximately 0.6 inch (15 mm); and the curvature, preferably in a single plane, is defined by a radius R, which may be approximately 0.2 inch, according to an exemplary embodiment. According to the illustrated embodiment, electrode 561 is located in close proximity to a distal tip 565 of extension 560, which tip 565 is preferably tapered. FIG. 5B illustrates distal tip 565 being slightly enlarged from a remainder of extension 560; and, according to some embodiments, tip 565 includes electrode 561, which forms at least a portion of the taper, and a relatively soft medical grade silicone rubber member 567, which may include a steroid embedded therein. The illustrated contour of electrode 561 may help electrode 561 to make better tissue contact when tip 565 lies adjacent to tissue, for example, as illustrated in FIG. 6C. According to an exemplary embodiment, a diameter of tip 565 (as shown in FIG. 5B) is approximately 0.07 inch (1.8 mm), and a surface area of electrode 561 is approximately 5.8 mm². Electrode 561 may be formed from a platinum iridium alloy.

FIG. 5B further illustrates pacing extension 560 being formed by a coiled multi-filar conductor 562 (e.g., MP35N alloy) enclosed within a jacket of insulation 564 (e.g., medical grade polyurethane), and an exemplary junction between electrode 561 and conductor 562, which may be secured by crimping and/or welding according to methods known in the art of implantable medical electrical leads. According to the illustrated embodiment, conductor 562 electrically connects electrode 561 to the aforementioned pulse generator contained within device housing 205, for example, via a feedthrough assembly constructed according to methods known in the art of implantable medical devices.

Turning now to FIGS. 6A, as was described above for device 200, device 500 is loaded into distal-most portion 332 of delivery tool 300 (FIG. 3), such that fixation fingers 230 are in the extended condition. It should be noted that fixation fingers 1230 may be substituted for fingers 230 in alternate embodiments. FIG. 6A illustrates fingers 230/1230 extending in a distal direction and alongside pacing extension 560 within distal-most portion 332. After device 500 is loaded, the operator may navigate delivery tool 300, with device 500 completely contained therein, through the patient's venous system, for example, from a femoral venous access site, up through the inferior vena cava IVC, and into a chamber of the heart, for example, the right atrium RA, as shown in FIG. 4A. In some preferred embodiments, pacing extension 560 extends distally beyond extended fingers 230/1230 so that the operator may withdraw deployment tube 330, per arrow W, just enough to expose electrode 561 out through distal opening 303 thereof, as shown in FIG. 6B. According to some exemplary embodiments, extension 560 can extend approximately 2 to 4 mm beyond opening 303 without fingers 230/1230 being exposed, so that the operator can advance tool 300 to one or more potential implant sites, where electrode 561 makes contact, to map electrical activity and/or to check pacing thresholds. According to some methods, after finding a desired implant site in this manner, the operator can pull back tool 300 and device 500 together, for example, to the position shown in FIG. 6B, and then retract deployment tube 330 even further, with respect to device 500 and inner member 320, to expose fixation fingers 230/1230 out from distal opening 303, thereby releasing fingers 230/1230 to the relaxed condition, for example, as illustrated in FIG. 4B. Then, as described above, the operator can advance tool 300 and device 500 together back to the desired implant site, for example, between pectinate muscle bands in right atrial appendage 102, and, thus, wedge the exposed fixation fingers 230/1230 between opposing tissue surfaces, as shown schematically in FIG. 6C for fingers 230, to hold device 500 at the implant site with electrode 561 making intimate tissue contact. With further reference to FIG. 6C, it may be appreciated that the length of pacing extension 560 serves to separate that portion of the implant site at which electrode 561 makes contact with that portion of the site at which fixation fingers 230 make spring contact (e.g., per bold arrows), so that any inflammation associated with the fixation fingers contact may not impair chronic pacing thresholds.

In the foregoing detailed description, the invention has been described with reference to specific embodiments. However, it may be appreciated that various modifications and changes can be made without departing from the scope of the invention as set forth in the appended claims.

We claim:

1. An implantable medical device comprising a housing, and a pacing electrode and a fixation member mounted in proximity to a distal end of the housing, the fixation member comprising a plurality of fingers spaced apart from one another around a perimeter of the housing, wherein each of the plurality of fingers is elastically deformable between a relaxed condition and an extended condition and comprises:
   a fixed end;
   a free end;
   one or more peripheral portions; and
   one or more cut-out portions, each cut-out portion of the one or more cut-out portions extending from a fixed end of the cut-out portion to a free end of the cut-out portion,
   wherein each peripheral portion of the one or more peripheral portions frames a respective cut-out portion of the one or more cut-out portions, whereby an inside edge of the peripheral portion is spaced apart from an outside edge of the cut-out portion, and wherein each peripheral portion of the one or more peripheral portions is integral with the respective cut-out portion of the one or more cut-out portions at the fixed end of the respective cut-out portion.

2. The device of claim 1, wherein each finger extends distally, when the finger is in the extended condition, so that the free end is located distal to the distal end of the housing.

3. The device of claim 1, wherein the fixation member further comprises a base ring, and each finger of the fixation member is integrally formed with the base ring.

4. The device of claim 1, wherein each of the fingers comprises:
   a first segment extending from the fixed end and being elastically deformable between a relaxed condition and an extended condition; and
   a second segment extending from the first segment to the free end.

5. The device of claim 4,
   wherein, in the relaxed condition, the first segment extends distally and outwardly from the fixed end and around a radius of curvature in a first direction; and
   wherein the second segment includes an inflection point from which the second segment extends around a radius of curvature in a second direction that is opposite the first direction of the first segment, so that the second segment extends proximally and away from the device housing to the free end, when the first segment is in the relaxed condition.

6. The device of claim 4, wherein the first segment comprises a first cut-out portion of the one or more cut-out portions and a first peripheral portion of the one or more peripheral portions.

7. The device of claim 6, wherein the second segment comprises a second cut-out portion of the one or more cut-out portions and a second peripheral portion of the one or more peripheral portions.

8. The device of claim 7, wherein the second segment comprises a third cut-out portion of the one or more cut-out portions and a third peripheral portion of the one or more peripheral portions.

9. The device of claim 8, wherein a length of the third cut-out portion is less than a length of the second cut-out portion.

10. The device of claim 6, wherein the fixed end of the first cut-out portion is located proximately to the fixed end of the finger.

11. The device of claim 4, wherein the first segment of each finger, in the relaxed condition, encloses an angle greater than approximately 135 degrees.

12. The device of claim 4, wherein the first segment of each finger, in the relaxed condition, extends in a compound curve.

13. The device of claim 1, wherein at least one cut-out portion of the one or more cut-out portions tapers from a first width at the fixed end of the cut-out portion to a second width located proximately to the free tip of the cut-out portion, and wherein the first width is greater than the second width.

14. The device of claim 13, wherein the free tip of the at least one cut-out portion is rounded, having a width greater than the second width.

15. The device of claim 1, wherein a width of at least one cut-out portion of the one or more cut-out portions is constant along a corresponding length.

16. The device of claim 1, wherein the one or more cut-out portions comprises a plurality of cut-out portions spaced apart from one another along a length of the finger.

17. The device of claim 16, wherein spacings of the plurality of cut-out portions relative to each of the fixed and free ends of the finger are configured to control the stiffness of the finger.

18. An interventional medical system comprising:
an implantable medical device comprising a housing, and a pacing electrode and a fixation member mounted in proximity to a distal end of the housing, the fixation member comprising a plurality of fingers spaced apart from one another around a perimeter of the housing, wherein each of the plurality of fingers is elastically deformable between a relaxed condition and an extended condition and comprises:
a fixed end;
a free end;
one or more peripheral portions; and
one or more cut-out portions, each cut-out portion of the one or more cut-out portions extending from a fixed end of the cut-out portion to a free end of the cut-out portion,
wherein each peripheral portion of the one or more peripheral portions frames a respective cut-out portion of the one or more cut-out portions, whereby an inside edge of the peripheral portion is spaced apart from an outside edge of the cut-out portion, and wherein each peripheral portion of the one or more peripheral portions is integral with the respective cut-out portion of the one or more cut-out portions at the fixed end of the respective cut-out portion; and
a delivery tool comprising a deployment tube, the deployment tube including a distal opening and a distal-most portion terminated by the distal opening, the distal-most portion being sized to contain the device and to hold the plurality of fingers in the extended condition.

19. The system of claim 18, wherein the fixation member further comprises a base ring, and each finger of the fixation member is integrally formed with the base ring.

20. The system of claim 18, wherein each of the fingers comprises:
a first segment extending from the fixed end and being elastically deformable between a relaxed condition and an extended condition; and
a second segment extending from the first segment to the free end.

21. The system of claim 20, wherein the first segment comprises a first cut-out portion of the one or more cut-out portions and a first peripheral portion of the one or more peripheral portions.

22. The system of claim 21, wherein the second segment comprises a second cut-out portion of the one or more cut-out portions and a second peripheral portion of the one or more peripheral portions.

23. The system of claim 22, wherein the second segment comprises a third cut out portion of the one or more cut-out portions and a third peripheral portion of the one or more peripheral portions.

24. The system of claim 23, wherein a length of the third cut-out portion is less than a length of the second cut-out portion.

25. The system of claim 22, wherein the fixed end of the first cut-out portion is located proximately to the fixed end of the finger.

26. The system of claim 20, wherein:
the first segment of each finger of the fixation member extends distally and outwardly from the corresponding fixed end and around a radius of curvature in a first direction, when the first segment is in the relaxed condition; and
the second segment of each finger of the fixation member includes an inflection point from which the second segment extends around a radius of curvature in a second direction that is opposite the first direction of the corresponding first segment, so that the second segment extends proximally and away from the device housing to the corresponding free end, when the corresponding first segment is in the relaxed condition.

27. The system of claim 20, wherein the first segment of each finger, in the relaxed condition, encloses an angle greater than approximately 135 degrees.

28. The system of claim 20, wherein the first segment of each finger, in the relaxed condition, extends in a compound curve.

29. The system of claim 18, wherein at least one cut-out portion of the one or more cut-out portions tapers from a first width at the fixed end of the cut-out portion to a second width located proximately to the free tip of the cut-out portion, and wherein the first width is greater than the second width.

30. The system of claim 29, wherein the free tip of the at least one cut-out portion is rounded, having a width greater than the second width.

31. The system of claim 18, wherein a width of at least one cut-out portion of the one or more cut-out portions is constant along a corresponding length.

32. The system of claim 18, wherein the one or more cut-out portions comprises a plurality of cut-out portions spaced apart from one another along a length of the finger.

33. The system of claim 32, wherein spacings of the plurality of cut-out portions relative to each of the fixed and free ends of the finger are configured to control the stiffness of the finger.

* * * * *